United States Patent [19]

Marcus

[11] Patent Number: 4,622,959
[45] Date of Patent: Nov. 18, 1986

[54] MULTI-USE FEMORAL INTRAMEDULLARY NAIL

[76] Inventor: Randall E. Marcus, 837 Nashville Ave., New Orleans, La. 70115

[21] Appl. No.: 708,393

[22] Filed: Mar. 5, 1985

[51] Int. Cl.$^4$ .............................................. A61F 5/04
[52] U.S. Cl. ........................... 128/92 YZ; 128/92 VD
[58] Field of Search ........... 128/92 BC, 92 BA, 92 B, 128/92 BB, 92 R, 92 G, 92 EB, 92 EC

[56] References Cited

U.S. PATENT DOCUMENTS

| | | | |
|---|---|---|---|
| 2,934,065 | 4/1960 | Townley | 128/92 CA |
| 3,067,740 | 12/1962 | Haboush | 128/92 CA |
| 3,433,220 | 3/1969 | Zickel | 128/92 CA |
| 3,670,724 | 6/1972 | Bosacco | 128/92 D |
| 3,782,373 | 1/1974 | Smythe | 128/92 EB |
| 3,814,089 | 6/1974 | Deyerle | 128/92 EB |
| 3,835,849 | 9/1974 | McGuire | 128/92 EB |
| 3,990,438 | 11/1976 | Pritchard | 128/92 BC |
| 4,103,683 | 8/1978 | Neufeld | 128/92 BA |
| 4,212,294 | 7/1980 | Murphy | 128/92 BC |
| 4,257,411 | 3/1981 | Cho | 128/92 EB |
| 4,310,931 | 1/1982 | Muller | 128/92 CA |
| 4,341,206 | 7/1982 | Perrett et al. | 128/92 EB |
| 4,381,770 | 5/1983 | Neufeld | 128/92 BA |
| 4,404,693 | 9/1983 | Zweymuller | 128/92 C |
| 4,418,422 | 11/1983 | Richter et al. | 128/92 EB |
| 4,423,721 | 1/1984 | Otte et al. | 128/92 EC |
| 4,475,545 | 10/1984 | Ender | 128/92 G |
| 4,541,424 | 9/1985 | Grosse et al. | 128/92 EB |

OTHER PUBLICATIONS

Richards Medical Co. Publication, "Russell Taylor Interlocking Nail System", 12 pages.
Richards Medical Co. Publication," Orthopaedic Product", 4 pages.

*Primary Examiner*—Robert P. Swiatek
*Assistant Examiner*—Cary E. Stone
*Attorney, Agent, or Firm*—Roy F. Hollander

[57] ABSTRACT

An intramedullary nail for use in fractures of the left or right femur includes a body having a head, an intermediate portion and a distal tip. Transverse openings are provided in the body near the distal tip and in the head for receiving locking screws. One opening in the head has its axis within the femoral neck and another opening has its axis generally transverse thereto. The nail head has a seat with a transverse locating slot for securing a screw insertion tool in a fixed angular position in which a screw guide on the tool is aligned with one of the screw receiving openings.

14 Claims, 8 Drawing Figures

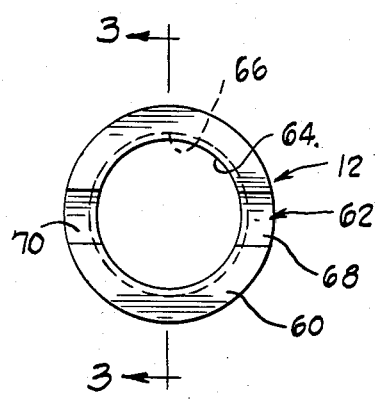
Fig. 4
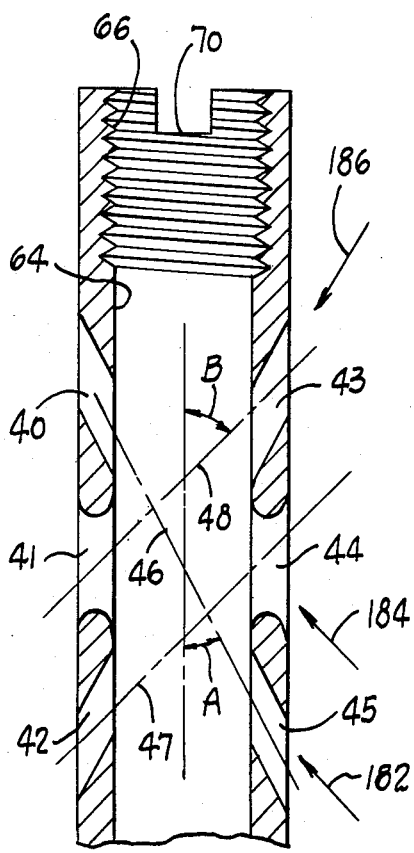
Fig. 3
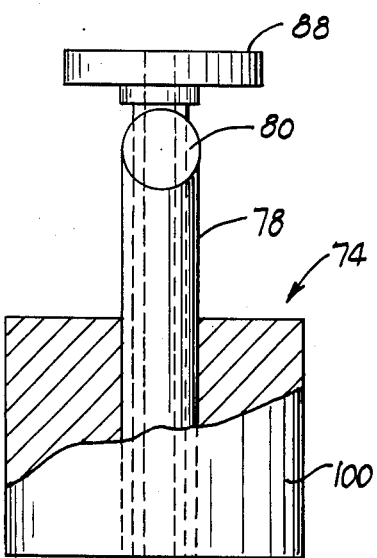
Fig. 5
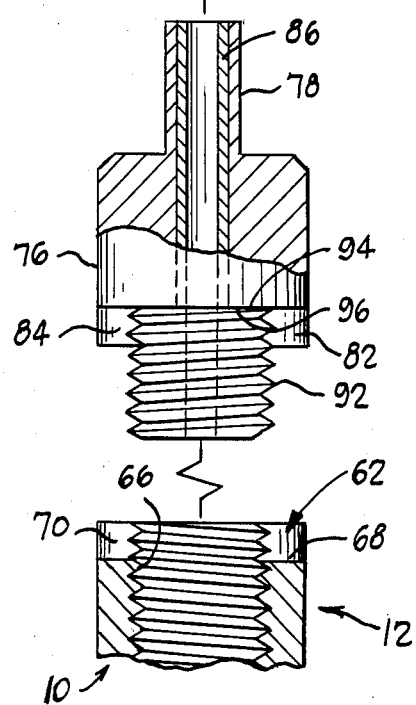

MULTI-USE FEMORAL INTRAMEDULLARY NAIL

This invention relates generally to femoral intramedullary nails or pins, and particularly, to an all-purpose or multi-use femoral intramedullary nail for use in fractures of the femur from the femoral neck to the supracondylar region. More particularly, the invention reduces the number of different nails required for various different fractures, which correspondingly reduces the possibility of selection of an unsuitable nail, as well as delays in performing fracture nailing surgery of the femur, because a particular nail is unavailable.

BACKGROUND OF THE INVENTION

Various intramedullary nails, particularly for use in repair of fractures of the femur, are known in the prior art.

Fractures of the femur can occur in any part of the femur from the femoral neck to the supracondylar region. Such fractures, in the past, have been particularly vexatious because of the required extended periods of time that the patient must be at least partly immobilized during the healing of such fractures. There is also a significant recovery period due to such extended immobilization.

In contrast, intrarmedullary nailing of femoral fractures permits the patient to apply weight to the involved leg within a day or two after surgery. Correspondingly, the technique of intramedullary nailing has found particular application in fractures of the femur.

Nails of different length are required for femoral nailing, depending on the location of the fracture and length of the femur of the patient. Nails of different diameters are also required to permit selection of a nail to fit the medullary canal of the patient after the usual procedure of reaming this canal, since a loose fit will not hold the fracture, and a very tight fit risks jamming in the bony tube. In the past, different nails and nailing arrangements have been used to repair fractures in different portions of the femur. This has required the surgeon to have available each of the different types of nails in each of the various required lengths and diameters, or delay operating until the proper nail or selection of nails can be obtained. Of further significance has been the need for the surgeon to acquire expertise in the use of and installation of these different types of prior art nails to repair fractures in different parts of the femur.

The use of such nails to surgically repair the femur requires reaming of the medullary canal to provide an appropriate opening to receive the nail. Pre-operative roentgenograms of the fractured femur and both adjacent joints are taken in two planes, usually at the same distance from the femur in an effort to determine the extent of damage and to provide a gauge for use in selection of an appropriate nail. It is however, desirable to have several nails of slightly different diameter and of different lengths available, since such gauging may not be completely accurate.

In the past, a femoral nail in the form of a slotted steel tube, sometimes referred to as the Kuntscher nail was driven into the medullary canal of the femur to repair fractures. The theory behind the Kuntscher intramedullary nail is that the slotted tube is transversely elastic, and is driven into a slightly smaller medullary canal thereby permitting the nail to lock by expansion in the medullary canal. It is, however, this transverse elasticity which causes difficulties in applications requiring a transverse screw, since the nail can also distort torsionally during insertion and the preformed screw or cross-nail receiving openings in the walls of the nail, particularly at the distal end, are often difficult to precisely locate. It is to be appreciated that the surgeon often works "blind" during the operation, since X-ray exposure must be maintained at a minimum, and the location of screw or transverse pin receiving openings in a twisted nail are often difficult to gauge even with several roentenograms. Should the location and angular disposition of the screw receiving openings in the inserted nail be misjudged or out of alignment with each other, insertion of the transverse screw becomes difficult and time consuming.

In addition to the Kuntscher nail, a number of other nails and techniques have been proposed for pinning or nailing fractures in various portions of the femur. As indicated above, however, in the past, different types of nails have been used for nailing of different portions of the femur. For example, where the fracture is in the femoral neck, one type of nail was used, and a different nail was used for a fracture of the intertrochanteric region, and yet a third type of nail was required for fractures in the distal femur region. As also indicated above, this required not only a different nail for the different fractures, but also required the surgeon to attain expertise in the use of each different nail.

Further, it was, in the past, necessary to have left and right nails for use in the left and right femoral neck fractures.

In summary, the available prior art nails have simply not been wholly satisfactory for repair of fractures of the femur.

SUMMARY OF THE INVENTION

In accordance with Applicant's invention, the intramedullary nail takes the form of a nail of closed cross-section, in contrast to the slotted transversely resilient Kuntscher nail. The configuration and cross-section of the nail along its length provides a nail which is quite rigid both axially and torsionally. The head or upper end of the nail includes a securing arrangement for securing a tool for driving and extracting the nail, and the tool advantageously cooperates with a locating slot in the head so that the desired angular disposition of the nail is indicated and easily maintained during insertion of the nail.

The nail is provided with several screw receiving openings at various locations along its length, and extending at selected angles relative to the axis of the nail so that the same nail can be used for repair of fractures of the femur from the femoral neck to the supracondylar region. In accordance with one aspect of the invention, the same nail can be used for fractures of the right or left femoral neck.

An additional feature of the nail of this invention is that after insertion of the nail in the femur, and removal of the driving tool, a jig can be secured to the head of the nail, to accurately locate and guide a drill or other cutting tool in precise alignment with any of the preformed screw receiving openings in the nail. This assures that the locking screws, when threaded through the femur, will precisely align with the openings in the nail without any additional drilling or reaming of the femur to attain alignment. Strong gripping of the screw in the femur (and the nail) as well as relatively rapid drilling and insertion of the screw or screws required, is thus assured.

In accordance with the invention, one or more jigs can be provided. Each jig, when secured to the head of the inserted nail is precisely aligned in a predetermined circumferential position relative to the nail. Each jig is provided with guides for guiding a drill or reamer precisely along the axis of one or more of the screw receiving openings of the nail. It is therefore assured that the screw opening formed in the femur precisely aligns with the axis of the opening in the nail so the locking screw can be quickly and accurately inserted.

In accordance with the invention, one jig is used for precisely locating the screw receiving openings in the head of the nail for fixation of either the femoral neck or the intertrochanteric region. A different jig can be used for locating the screw receiving openings in the distal femur region. With either jig, securing the jig to the head of the inserted nail automatically aligns one or more guides of the jig precisely with the axis of the screw opening to be used. The jig for the distal femur region can be adjustable for use with nails of different length, and to form openings for the several screws which are sometimes required for locking the nail in this region.

Since the femur curves slightly along its length, it is preferred that the nail have a similar long radius of curvature of, for example, 50 inches. It is necessary, however, that the nail be oriented angularly during insertion so that its curvature is aligned with the curvature of the femur. By virtue of the orientation indicating arrangement on the tool for inserting and driving the nail, the surgeon can accurately orient and maintain such angular orientation of the nail as it is inserted and driven into the medullary canal of the femur.

In accordance with the invention, the nail is hollow and of somewhat different cross-section along its length. The head of the nail is generally cylindrical in the intertrochanteric region, an intermediate body portion of the nail is of closed, generally clover-leaf section, and the lower or distal tip of the nail can be of clover-leaf or of a generally scalloped cylinder exterior configuration. This provides a nail which is very rigid both axially and torsionally, yet can flex slightly along its length and can also yield slightly radially along its intermediate body portion. This permits the nail to accommodate itself to slight differences between the curvature of the medullary canal and the curvature of the nail itself. By virtue of its closed tubular clover-leaf or scalloped configuration, the nail is quite rigid torsionally, which assures that the screw receiving openings in the distal tip do not displace circumferentially (relative to the head) during insertion of the nail, to enable precise and accurate drilling and insertion of the locking screw in any of the screw receiving openings of the distal tip.

In accordance with the invention, the same nail can be used in fractures of the left or right femur, including fractures of the right or left femoral neck. Correspondingly, in accordance with the invention, the number of different types of nails required for different fractures of the femur is vastly reduced, the possibility of inadvertently using a left nail in a fracture of the right femur and vice versa is eliminated, and the surgeon need only acquire expertise in working with a single type of nail in order to repair fractures in any part of the femur.

Additional features, objects, and advantages of the invention will become apparent from the drawings and the detailed description of the preferred embodiment.

BRIEF DESCRIPTION OF THE DRAWINGS

FIG. 3 is an enlarged view in axial section of the head of the nail taken along line IV—IV of FIG. 4;

FIG. 4 is an enlarged top plan view of the head of the nail;

FIG. 5 is a front view in elevation, with portions cut away for purposes of illustration, of a slide hammer extractor-driver tool which can be used to insert and remove the nail;

DETAILED DESCRIPTION

Figure 1:
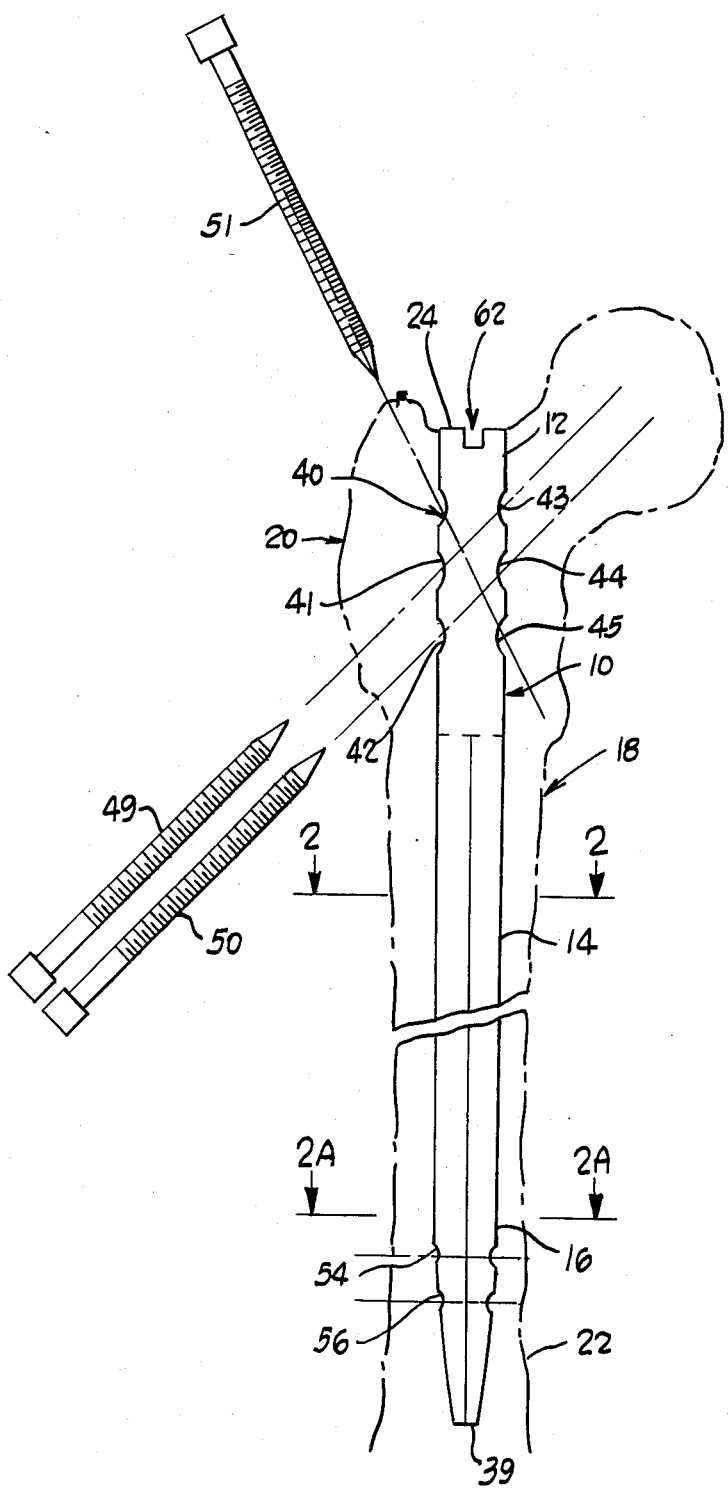
FIG. 1 is a front view in elevation of an intramedullary nail according to the invention, within a right femur (shown in phantom lines) and also showing fixation and femoral neck screws insertable into the nail.

FIG. 1 shows the improved intramedullary nail 10, according to the invention. The nail 10 takes the form of an elongated unitary or integral hollow body having a head 12, an intermediate body portion 14, and a distal tip portion 16.

As shown at FIG. 1, the nail is insertable into the medullary canal of a femur 18 (shown in phantom lines) to a position in which head 12 is in the intertrochanteric region 20 of the femur, and the distal tip 16 is in the distal femur region 22.

The nail 10 is hollow, along its length, to provide an axial opening which extends the length of the nail, and through the upper end of the head 12 and the lower end of the distal tip 16. In contrast to the prior art Kuntscher nail, the nail 10 has a continuous circumferential sidewall whereas the Kuntscher nail has a longitudinal slot in the sidewall extending the length of the nail.

Advantageously, in accordance with the invention, the cross-sectional configuration of the sidewall of the nail is different at different locations along its length. The head 12 is preferably of circular exterior configuration, and of a length to extend to the lower portion of the intertrochanteric region, when the nail is fully inserted into the femur with its upper end 24 adjacent the upper femoral tip, as shown at FIG. 1. The head 12 can taper slightly inwardly along its length, or can be substantially cylindrical along its length.

Figure 2A:
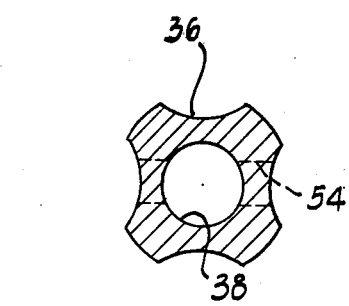
FIG. 2A is an enlarged view taken in section along line IIA—IIA of FIG. 1 and showing one preferred form of the cross-section of the nail in the region of its distal tip.
Figure 2:
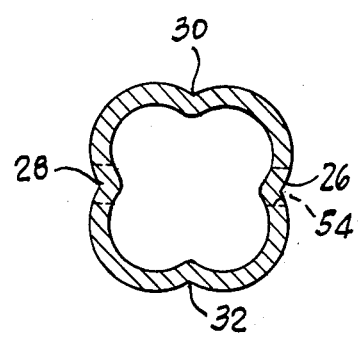
FIG. 2 is an elongated view in section taken along line II—II of FIG. 1 and showing the cross-section of the intermediate body portion of the nail.

As shown at FIG. 2, the intermediate body portion 14 of the nail has a cross-sectional configuration of generally clover-leaf form. This configuration includes opposed diametrically inwardly extending indentations 26 and 28. There are also opposed diametrically inwardly extending indentations 30 and 32 lying on a diameter at right angles to the plane of the indentations 26 and 28.

As shown at FIG. 2, it is preferred that the wall thickness of the sidewall be essentially the same at the curved leaf portion as it is at the indentations.

The distal tip 16 can have the same generally cloverleaf configuration as the intermediate body portion 14. As an alternative, the distal tip can have the scalloped configuration shown at FIG. 2A. This scalloped configuration includes four equidistantly spaced round bottom grooves or flutes 36 formed in the outside surface of the nail in the region of the distal tip 16. When the scalloped configuration is used, the distal tip has a generally cylindrical bore 38. The configuration of FIG. 2A finds advantage for use in a relatively small diameter nail and provides an increased wall thickness for receiving transverse screws to be inserted through the nail in the region of the distal tip, as will soon be described.

A nail 10 of average size has a diameter of 14 mm, and a length of about 42 cm. The head 12 of such a nail has a sidewall thickness of about 2 mm with the sidewall of the intermediate body portion the same or slightly thinner. The distal end tapers along about 8 cm to facilitate insertion and its wall thickness becomes 1 mm or less. The diameter of the exit opening 39 through the lower end is on the order of 5 mm to permit threading the nail along a guide rod or pin inserted in the medullary canal and which is used as a guide for reaming the canal and where reduction of the fracture is required. The wall thicknesses of the nail will be slightly greater for a larger diameter nail and slightly smaller for a smaller diameter nail.

Referring to FIG. 1, the nail 10 is advantageously driven into the femur to a position in which the top end of head 12 is adjacent to and preferably flush with the entry opening formed in the fermoral tip. Formed in the sidewall of head 12 are several screw receiving openings 40-45.

As shown at FIG. 3, opening 40 is diametrically opposed to opening 43, opening 41 is diametrically opposed to opening 44, and opening 42 is diametrically opposed to opening 45. A line 46 extending through the centers of openings 40 and 45 makes an angle A of about 30° with the axis of the nail. Lines 47 and 48 extending through the centers of openings 41, 43 and openings 42, 44, respectively, each make an angle B of about 45° with the axis of the nail, which corresponds generally to the angle of the axis of the femoral neck.

For fractures of the femoral neck of the right femur, screws such as screws 49, 50 are inserted upwardly through openings 41, 43, and openings 42, 44, respectively. For locking the nail in the intertrochanteric region of the right femur a screw, such as screw 51, is inserted downwardly through the openings 40, 45. Screw 51 is not used where the screws 49 and 50 are required. The centers of the openings 40-45 are all in a common vertical plane passing generally through the axis of the femoral neck.

Several internally threaded transverse screw receiving openings are formed in the distal tip. FIG. 1 shows two such openings 54 and 56. Openings 54 and 56 extend diametrically of the nail and are vertically spaced apart. While only two openings are shown, additional openings can be provided. The axes of openings 54 and 56 are in essentially the same vertical plane as the centers of the openings 40-45.

Since the medullary canal of the femur is usually of a long radius curvature, the nail 12 preferably has a radius of curvature of 50 inches. This curvature is about a point behind the nail as viewed at FIG. 1, i.e. the femur curves anteriorly.

As shown at FIGS. 4 and 5, the top end of head 12 presents a flat seat 60. Formed in the top of the head is a diametrically extending U-shaped slot 62. The slot 62 preferably has its axis extending along a diameter perpendicular to the plane containing the axes of the several screw receiving openings namely, openings 40-45, 54, and 56. As will soon be explained, this slot provides a means for angularly orienting the nail, and for accurately locating a tool with respect to the nail and the several screw receiving openings.

Slot 62 has a width somewhat less than the diameter of the opening 64 in head 12. Opening 64 has internal threads 66 for threadedly securing various tools to the head of the nail both before and after insertion of the nail in the femur. As can be seen at FIG. 4, the slot 62 provides locating grooves 68 and 70 at opposite sides of opening 64.

FIG. 5 shows an extractor-driver 74 for removing a nail 10 from the femur and for driving the nail into the femur. At the lower end of the driver is a seat 76 rigid with a sleeve 78, and a cross-handle 80 is secured to the upper end of sleeve 78. Projecting downwardly from bottom face 82 of seat 76 are diametrically aligned rectangular lugs 82 and 84. These lugs are each of a width to be a close fit in the respective grooves 68 and 70 formed by the slot 62 in the end of head 12. Extending through seat 76 and sleeve 78 is a rotatable sleeve 86, which extends through handle 80 and is secured to a knob 88, at the extreme upper end of the tool. Fixed to the lower end of sleeve 86 is a threaded screw 92 having threads to mate with the internal threads 66 in the head of nail 12. As shown at FIG. 5, screw 92 has an upwardly facing shoulder 94 which seats against a transverse annular shoulder 96 at the bottom of seat 76. The knob 88 has only a slightly axial clearance relative to the handle 80, so that rotating the knob 88 threads stud 92 into the threaded opening in the head of the nail. As screw 92 is tightened, with lugs 82 and 84 aligned with the respective grooves 68 and 70, the seat member 76 is pulled down and tightly seated on the head 12 of the nail.

Extending around sleeve 78 is a cylindrical slide hammer 100 which can be slid downwardly against the top of seat 76 for driving the nail into the femur, and can be slid upwardly to impact against the bottom of handle 80 to assist in extracting or withdrawing a nail 10 from the femur. It is to be noted that the lugs 82 and 84 preferably lie along a diameter perpendicular to the direction of extension of handle 80. Correspondingly, since the direction of slot 62 is known relative to the plane of the axes of the several screw receiving openings, the handle 80 acts as an indicator to indicate the precise angular orientation of nail 10 when the extractor driver is secured to the head of the nail.

Figure 6:
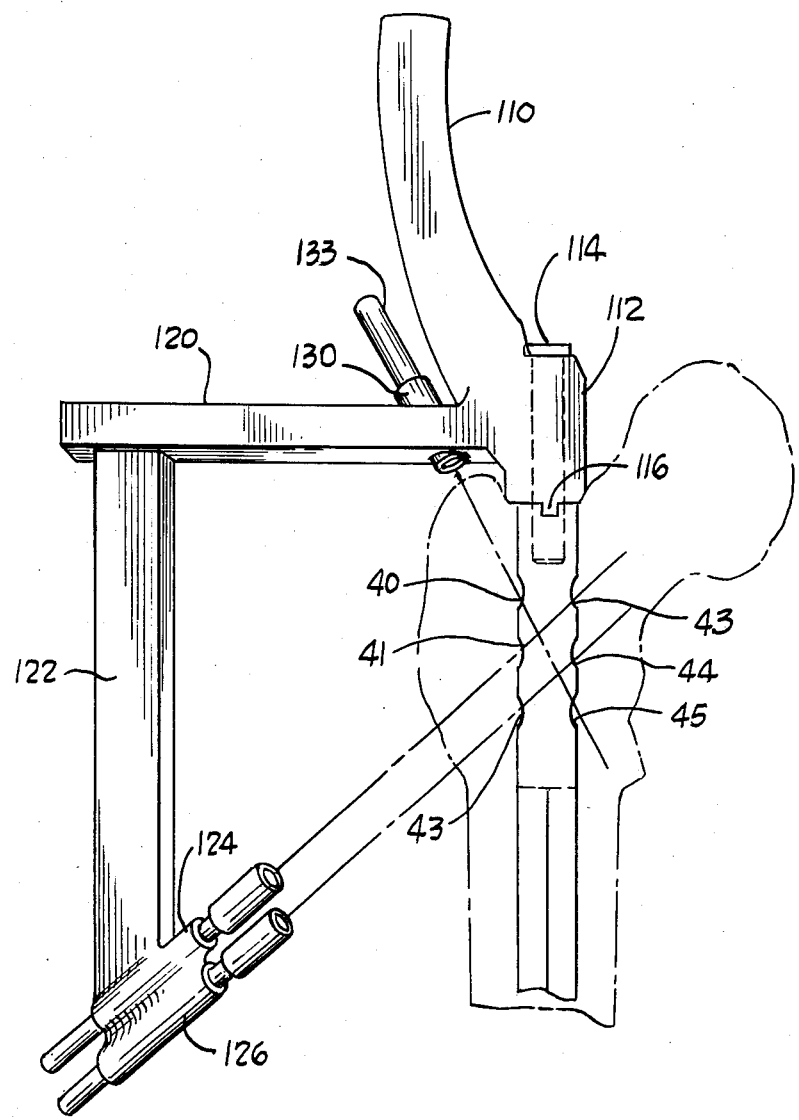
FIG. 6 is a view in front elevation of a first jig, in accordance with the invention, for use in drilling and/or inserting screws in the proximal region of the femur in alignment with openings in an inserted nail.

FIG. 6 shows a screw guide and drilling jig for accurately forming screw receiving openings in the proximal region of the femur, in alignment with required ones of the openings 40-45 in the head of the nail, after the nail is inserted in the femur of a patient. The jig is formed from rectangular bar stock and has a handle 110 to facilitate manipulation. At one end of the handle is a securing head 112, the lower end of which has a configuration identical to seat 76 of the driver-extractor. Extending through head 112 is a fastening screw having threads to mate with the internal threads 66 in the head 12 of the nail. The lugs 116 at the bottom of head 112 enter the respective grooves in the upper end of the nail head to accurately align the jig circumferentially as well as axially of the inserted nail, when the screw 114 is fully tightened.

Extending laterally from head 112 is a bar 120, and secured to bar 120 and projecting downwardly is a guide arm 122. Fixed to the lower end of guide arm 122 are guide sleeves 124 and 126, the axes of which are in precise diagonal alignment with the centers of openings 41, 43 and 42, 44. Slidable within sleeves 124 and 126 are removable bushings which can be extended into the thigh of the patient to prevent damage to soft tissue during drilling or insertion of the screws for repair of the femoral neck.

Fitted into bar 120 is a guide sleeve 130 which is in precise axial alignment with the centers of openings 40, 45 in the inserted nail, when the jig is secured to the nail. An extension bushing 133 slidable through sleeve 130 can also be provided for more accurate guiding of either a drill for forming the opening in the femur, or for guiding the screw during insertion.

Figure 7:
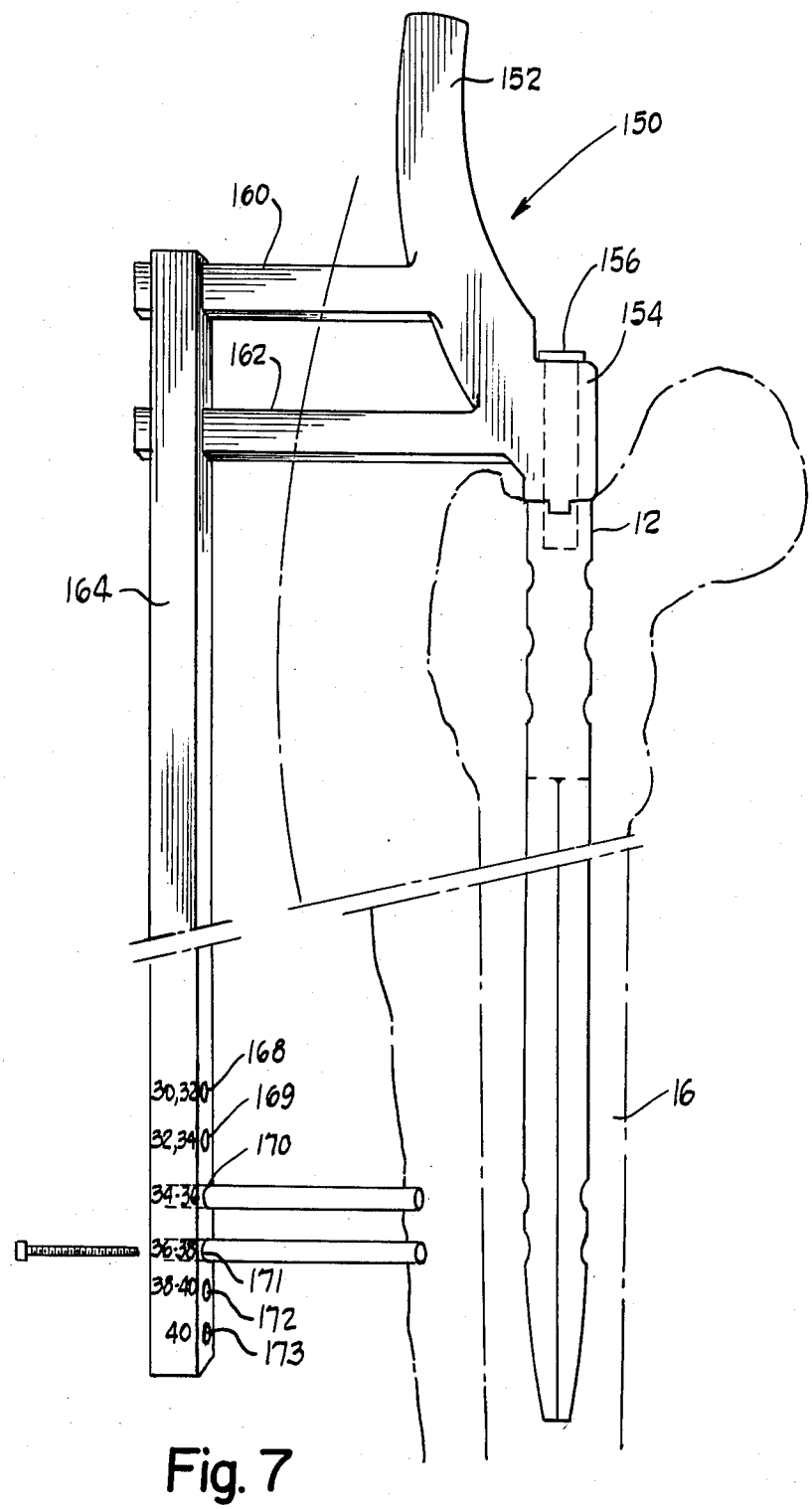
FIG. 7 is a view in front elevation of another jig in accordance with the invention for use in drilling and/or inserting screws, in alignment with distal screw openings of an inserted nail.

FIG. 7 shows a jig 150 for accurately forming locking screw receiving openings in the femur in alignment with the preformed threaded screw receiving openings in the distal tip 16 of the nail. Jig 150 includes a manipulating handle 152 extending upwardly from head 154, the lower end of which is substantially identical to seat 76 of the extractor-driver. A screw 156 with threads that mate with the threads in the end of head 12 of the nail extends through head 154 and secures jig 150 to the inserted nail when screw 156 is tightened. By virtue of the locating lug and slot arrangement, securing jig 150 to the inserted nail automatically positions the jig both angularly and axially of the inserted nail.

Projecting from handle 152 are two guide bars 160 and 162 which are parallel to each other and extend into rectangular openings in the upper end of a bar 16. Bar 164 is slidable inwardly and outwardly on bars 160 and 162 to permit positioning the bar 164 at a desired position relative to the thigh 166 of the patient.

At the lower end of bar 164, there is a plurality of guide openings 168-173. These openings are each spaced apart the same distance as corresponding openings in a nail and are appropriately marked with length indicia. As shown, guide sleeves are inserted in two of the openings which are in alignment with the openings in the distal tip of the inserted nail. The other openings are provided for use with nails of different length from the nail shown, to permit use of the same jig with such nails of different length which will have the openings either further up or further down relative to the openings shown.

The description above relates to repairs of fractures of the right femur, with the nail 10 of this invention. The same nail 10 can also be used for fractures of the left femur. The left femur is a mirror image of the right femur shown at FIGS. 1, 6 and 7. The left femur is also anteriorly curved. It is therefore not possible to rotate the nail 10 180° from the position shown at FIGS. 1, 6 and 7 for use in the left femur. Instead, for fractures of the left femur the nail 10 is inserted in the medullary canal of the left femur with the same orientation shown at FIG. 1.

For fractures of the femoral neck of the left femur, screws are inserted upwardly through openings 45, 41 and 44, 40 as shown by the arrows 182 and 184 (FIG. 4). To lock the nail in the intertrochanteric region of the left femur, a screw is inserted downwardly through openings 43, 42, as indicated by arrow 186.

Such use of the nail in either the right or left femur is permitted because the nail is symmetrical about a vertical plane perpendicular to the axis of the femoral neck.

To facilitate insertion of screws through the pair of openings 40, 45 it is preferred that these openings, when the nail is made, be bored (or reamed) along an axis 46 at an angle A which is about 30°. The openings 43, 42 are formed along an axis which slopes in the opposite direction, as shown at FIG. 4 by arrow 186.

To facilitate insertion of the screws 49 and 50 upwardly through openings 41, 43 and 42, 44 in the right femur, as well as upwardly through openings 44, 40 and 45, 41 when used in the left femur, each of the openings 40-45 can also be reamed along the several axes along which a screw could be inserted. Correspondingly, during manufacture of the nail, openings 42, 44 are reamed along the axis of line 47, and openings 41 and 43 are reamed along the axis of arrow 182, and openings 44, 40 are reamed along the axis of arrow 184.

As an alternative, the openings 40-45 can be elongated vertically i.e. the openings are elliptical with the major axis of the ellipse in a vertical plane including the axis of the nail.

While the angles A and B (FIG. 4) have been indicated to be 30° and 45°, respectively, angle A can be from 27° to 32°, and angle B can be from about 43° to 48°.

The screws used in the openings 40-45 are preferably self-threading screws, but these openings can be partly pre-threaded in the required directions.

To avoid possible outward distortion of the metal of the nail by a self-tapping screw as it is inserted through any pairs of the openings 40-45, each of these openings can be slightly dimpled inwardly, or can be slightly countersunk. Rough edges which could interfere with removal of the nail are thus avoided.

The jigs of FIGS. 6 and 7 can be used to form the required screw receiving openings in the left femur, by securing the tools to the head of a nail inserted in the left femur, but with the respective jigs rotated 180° from the positions shown at FIGS. 6 and 7.

Stainless steel or titanium are preferred materials for the nail.

While preferred embodiments of the nail and tools in accordance with this invention have been shown and described, changes and variations can be made without departing from the scope of this invention.

I claim:

1. An intramedullary nail for use in fractures of the femur comprising, an elongated unitary body having a head, an intermediate body portion, and a distal tip, said body having an axial opening therein extending through said head and into said intermediate body portion, said nail being insertable into the medullary canal of a femur to a position in which said distal tip is in the distal femur region and said head is in the intertrochanteric femur region, a first transverse screw receiving opening in said body near said distal tip, a second screw receiving opening in said head having its axis within the femoral neck, and a third screw receiving opening in said head having an axis generally transverse to the axis of the femoral neck and crossing the axis of the second opening, means for securing an inserting tool to said head for inserting the nail in a femur, and means on said head defining a line having a predetermined fixed angular relation to the axis of each of said screw receiving openings for accurately locating a guide of a tool circumferentially and axially of the nail in precise axial alignment with any of said openings.

2. An intramedullary nail according to claim 1 wherein the axes of each of said screw receiving openings are substantially in a common vertical plane passing through the axis of the nail.

3. An intramedullary nail according to claim 1 comprising at least two transverse parallel screw receiving openings in the region of said distal tip.

4. An intramedullary nail according to claim 1 wherein each of said screw receiving openings comprises an internally threaded opening.

5. An intramedullary nail according to claim 1 wherein said means for securing a tool to said head comprises internal threads in the axial opening in said head, and a seat for the tool on said head.

6. An intradmedullary nail according to claim 1 wherein said head comprises a head of circular exterior configuration.

7. An intramedullary nail according to claim 1 wherein said distal tip comprises a tapered end of the nail.

8. An intramedullary nail according to claim 1 wherein said intermediate body portion is of clover-leaf section along its length.

9. An intramedullary nail according to claim 1 wherein said nail curves anteriorly, said openings in said head have their axes in a common plane, and said openings in said head are symmetrical about a plane normal to said common plane.

10. An intramedullary nail according to claim 1 including a seat for a tool on said head, said seat having a transverse locating slot therein, the axis of said slot having a predetermined fixed angular relation to the axis of each of said screw receiving openings, said slot comprising said tool guide locating means.

11. An intramedullary nail according to claim 10 wherein said slot further comprises means for accurately locating a driver tool in a predetermined angular position on said head.

12. An intramedullary nail according to claim 1 wherein said intermediate body portion has a continuous circumferential sidewall throughout its length.

13. An intramedullary nail according to claim 1 in combination with a tool for aligning a screw guide with the axis of one of said screw receiving openings, said tool comprising a head engaged with the head of said nail in a predetermined fixed angular relation, a member extending from said tool head and connected thereto in fixed angular relation, a screw guide carried by said member extending toward said nail, the angular relation of said tool head to said nail head being such that said screw guide is aligned with the axis of one of said screw receiving openings.

14. A combination according to claim 13 including a seat for said tool on said nail head, said seat having a transverse locating slot, and a projection on said tool head engaged with said slot to position said tool head so that said screw guide is aligned with the axis of one of said screw receiving openings.

* * * * *